US008005712B2

(12) United States Patent
von Davier et al.

(10) Patent No.: US 8,005,712 B2
(45) Date of Patent: Aug. 23, 2011

(54) SYSTEM AND METHOD FOR LARGE SCALE SURVEY ANALYSIS

(75) Inventors: Matthias von Davier, Lawrenceville, NJ (US); Xueli Xu, Chicago, IL (US); Kentaro Yamamoto, Lawrenceville, NJ (US)

(73) Assignee: Educational Testing Service, Princeton, NJ (US)

( * ) Notice: Subject to any disclaimer, the term of this patent is extended or adjusted under 35 U.S.C. 154(b) by 979 days.

(21) Appl. No.: 11/697,650

(22) Filed: Apr. 6, 2007

(65) Prior Publication Data

US 2008/0021576 A1    Jan. 24, 2008

Related U.S. Application Data

(60) Provisional application No. 60/744,373, filed on Apr. 6, 2006.

(51) Int. Cl.
G06F 17/30 (2006.01)
(52) U.S. Cl. .......................................... 705/10
(58) Field of Classification Search ............ 705/10, 705/7.41
See application file for complete search history.

(56) References Cited

U.S. PATENT DOCUMENTS

| 5,059,127 | A * | 10/1991 | Lewis et al. ............... 434/353 |
| 6,144,838 | A | 11/2000 | Sheehan |
| 6,301,571 | B1 | 10/2001 | Tatsuoka |
| 6,322,366 | B1 * | 11/2001 | Bergan et al. ............ 434/118 |
| 2002/0128884 | A1 * | 9/2002 | Heching et al. ............ 705/7 |
| 2003/0232314 | A1 | 12/2003 | Stout et al. |
| 2004/0202987 | A1 | 10/2004 | Scheuring et al. |
| 2005/0222799 | A1 | 10/2005 | Bolt et al. |
| 2006/0003303 | A1 * | 1/2006 | Almond et al. ............ 434/322 |
| 2006/0014129 | A1 | 1/2006 | Coleman et al. |
| 2006/0035207 | A1 * | 2/2006 | Henson ..................... 434/350 |
| 2006/0099561 | A1 * | 5/2006 | Griph ........................ 434/322 |
| 2008/0076108 | A1 | 3/2008 | Von Davier et al. |

OTHER PUBLICATIONS

McGlohen, Meghan Kathleen; "The Application of a Cognitive Diagnosis Model via an Analysis of a Large-Scale Assessment and a Computerized Adaptive Testing Administration". May 2004. Univeristy of Texas at Austin.*
Rost, Jurgen; A logistic mixture distribution model for polychotomous item responses; British Journal of Mathematical and Statistical Psychology; vol. 44; 1991; pp. 75-92.
Andrich, David; Rasch Models for Measurement; Sage University Papers, Quantitative Applications in the Social Sciences; 2002; No. 07-068.
Yamamoto, Kentaro; Hybrid Model of IRT and Latent Class Models; Research Report, Educational Testing Service; Sep. 1989; New Jersey.
Yamamoto, Kentaro; A Model That Combines IRT and Latent Class Models; University of Illinois; 1987; Illinois.
Andrich, David; An Extension of the Rasch Model for Ratings Providing Both Location and Dispersion Parameters; Psychometrika vol. 27, No. 1; Mar. 1982; pp. 105-113.

(Continued)

*Primary Examiner* — Peter Choi
(74) *Attorney, Agent, or Firm* — Jones Day

(57) ABSTRACT

Disclosed herein is a method of analyzing large scale survey results comprising obtaining a sparse data set representing a subset of an original data set comprising a plurality of individuals' responses to a plurality of questions, wherein the sparse data set comprises less than ninety percent of the responses in the original data set; analyzing the sparse data set using a general diagnostic model; and obtaining estimated person parameters using the general diagnostic model.

18 Claims, 1 Drawing Sheet

OTHER PUBLICATIONS

Kelderman, Hendrikus; Loglinear Rasch Model Tests; Psychometrika vol. 49, No. 2; Jun. 1984; pp. 223-245.

Rost, Jurgen; Rasch Models in Latent Classes: An Integration of Two Approaches to Item Analysis; Applied Psychological Measurement; vol. 14, No. 3; Sep. 1990; pp. 271-282.

Masters, Geoff N.; A Rasch Model for Partial Credit Scoring; Psychometrika; vol. 47, No. 2; Jun. 1982; pp. 149-174.

Von Davier, M.; A General Diagnostic Model Applied to Language Testing Data; Princeton: Educational Testing Service; ETS RR-05-16; Sep. 2005.

Von Davier, M., Yamamoto, K.; Partially Observed Mixtures of IRT Models: An Extension of the Generalized Partial Credit Model.

Von Davier, M., Yamamoto, K.; A Class of Models for Cognitive Diagnosis—and Some Notes on Estimation; ETS Tucker Works Seminar; Princeton, NJ; Dec. 2, 2004.

Maris, E.; Estimating Multiple Classification Latent Class Models; Psychometrika; 64(2); pp. 187-212; 1999.

Muraki, E.; A Generalized Partial Credit Model: Application of an EM Algorithm; Applied Psychological Measurement; 16(2); pp. 159-176; 1992.

Von Davier, M., Yamamoto, K.; Mixture Distribution and Hybrid Rasch Models; In M. von Davier & C.H. Carstensen (Eds.), Multivariate and Mixture.

Xu, X., Von Davier, M.; Cognitive Diagnosis for NAEP Proficiency Data; Princeton: New Jersey; ETS RR-06-08; 2006.

Von Davier, M., Rost, J.; Mixture Distribution Item Response Models; Handbook of Statistics, vol. 26; pp. 643-661; Jul. 2005.

Vermunt, J.K.; Multilevel Latent Class Models; Sociological Methodology; vol. 33; No. 1; pp. 213-239; Jan. 2003.

Von Davier, M.; Mixture Distribution Diagnostic Models; Princeton: Educational Testing Service; ETS RR-07-32; Jul. 2007.

* cited by examiner

SYSTEM AND METHOD FOR LARGE SCALE SURVEY ANALYSIS

REFERENCE TO RELATED APPLICATION

This application claims priority to U.S. Application Ser. No. 60/744,373, filed Apr. 6, 2006, entitled "DIAGNOSTIC MODELS FOR LARGE SCALE SURVEY ANALYSIS," the entire contents of which is incorporated by reference herein.

BACKGROUND OF INVENTION

Item Response Theory (IRT) is a body of theory used in the field of psychometrics. In IRT, mathematical models are applied to analyze data from tests or questionnaires in order to measure abilities and attitudes studied in psychometrics. An IRT model is a mathematical function that specifies the probability of a discrete outcome, such as a correct response to an item, in terms of person and item parameters. Person parameters may, for example, represent the ability of a student. Items may be questions that have incorrect and correct responses, or statements on questionnaires that allow respondents to indicate level of agreement, or any number of other questions. IRT may be used to evaluate how well assessments work, or how well individual questions on an assessment work, to evaluate the characteristics the test or questionnaire is designed to evaluate. In education and testing, IRT may be used to develop and refine exams, maintain banks of items for exams, and compare the difficulty of different versions of exams.

Mixture distribution models are a set of IRT models that assume that the observed item response data are sampled from a composite population, that is, a population that consists of a number of components or subpopulations. In contrast to multigroup models that assume a known partition of the population and use an observed grouping variable to model the item response data, mixture distribution models do not usually assume that the mixing variable is observed, but rather offer ways to collect evidence about this variable my means of model assumptions and observed heterogeneity in this data.

The components of a mixture distribution can be distinguished by the differences between the parameters of the assumed distribution model that governs the conditional distribution of the observed data. In the case of item response data, it may be assumed that different parameter sets hold in different subpopulations. Or, in even more heterogeneous mixtures, different item response models may hold in different subpopulations.

Several IRT models will hereinafter be discussed. Latent class analysis (LCA) is an older IRT model. The model equation of LCA is:

$$P(x_1, \ldots, x_I) = \sum_{c=1}^{C} \pi(c) \prod_{i=1}^{I} p_{ci}(x_i) \quad \text{Equation 1}$$

In Equation 1, $x_1, \ldots, x_I$ represents the observed variables, c represents the (unobserved) mixing variable and may be interpreted as representing the indicator of populations, the $\theta$ variable is an (unobserved) latent variable that often represents ability, proficiency or other constructs in educational and psychological applications of latent variable models, such as item response theory. Let $\pi(c)$ be the count density of c and the conditional density of $\theta$ given c is $\phi(\theta|c)$. Finally, let the $p_{ci}(x|\theta)$ term denote the conditional probability of response x to item i given $\theta$ in population c. LCA is called a discrete model because it assumes the independence of response variables $x_1, \ldots, x_I$, so that:

$$p(x_1, \ldots, x_I) = \prod_{i=1}^{I} p_{ci}(x_i) \quad \text{Equation 2}$$

In the LCA, the conditional response probabilities are constrained to be the same for all members of a given class (subpopulation) c, but are allowed to differ across subpopulations.

It is often convenient to reparameterize the model equation in order to avoid the estimation bound probability-based parameters. A useful approach is to express the conditional probabilities as:

$$p_{ci}(x) = \frac{\exp(\beta_{cix})}{1 + \sum_{y=1}^{M_i} \exp(\beta_{ciy})} = \exp(\beta_{cix} - \delta_{ci}) \quad \text{Equation 3}$$

with $$\delta_{ci} = \ln\left[1 + \sum_{y=1}^{M_i} \exp(\beta_{ciy})\right].$$

This reparameterization does not change the model assumpation, but makes it easier to estimate parameters when additional constraints are to be met. One constrained model derived from the unconstrained LCA in Equation 1 is of particular importance for the derivation of mixture IRT models. The central idea is to disentangle item effects and group effects which are confounded in the $\beta_{cix}$ parameters and therefore require a relatively set of parameters for each latent class. This means that many parameters have to be estimated in each class, and therefore, the accuracy of these estimates will deteriorate when more classes are added to an existing model. A more parsimonious approach can be taken when using a linear decomposition of $\beta_{ixc}$ into item and class parameters such as $\beta_{ixc} = x(b_i\theta_c - \alpha_{ix})$ for decomposition into one class-level parameter and an item-category parameter, or $\beta_{ixc} = x(b_i\theta_c - a_i)$ which yields a model that shares features with a 2PL IRT model (i.e., a two-parameter logistic IRT model). These linear compositions greatly reduce the number of necessary parameters. A practical advantage of the linear decomposed version of the LCA is that each latent class is assigned an "ability level" $\theta_c$ and each item has one parameter or set of parameters (i.e., $a_{ix}$ or $(a_i, b_i)$ in the examples above) that stay the same across latent classes.

The Mixed Rasch model (MRM) is another IRT model. The MRM was developed after different response styles and test taker strategies were observed. MRM was developed with the goal of integrating the quantitative ability differences into modeling student populations by means of qualitative differences (e.g., quality or strategy). The Rasch and LCA models share the local independence assumption, but use quite different variables upon which to condition. In the Rasch model, a count of correct responses is sufficient for estimating the ability parameter, whereas the LCA assumes that an unobserved nominal variable that is more or less implicitly defined by class profiles explains all observed dependencies in the data. The model equation for the mixed Rasch model is:

$$P(x_1, \ldots, x_I) = \pi_r \frac{\exp\left[\sum_{i=1}^{I} \beta_i x_i\right]}{\gamma(r)} \quad \text{Equation 4}$$

where $\gamma(r)$ represents the symmetric function of order r. This function is defined as:

$$\gamma(r) = \sum_{\{(x1,\ldots,xI): \sum xi = r\}} \exp\left[\sum_{i=1}^{I} \beta_i x_i\right] \quad \text{Equation 5}$$

The Rasch model in a conditional form may be augmented by including provisions to estimate the model parameters at subpopulation level and to combine these subpopulations in a discrete mixture distribution. Consistent with the above definition of a discrete mixture distribution we may define:

$$P(x_1, \ldots, x_I \mid c) = \pi_{r|c} \frac{\exp\left[\sum_{i=1}^{I} \beta_{ixc}\right]}{\gamma_c(r)} \quad \text{Equation 6}$$

Then, for the marginal probability of a response vector:

$$P(x_1, \ldots, x_I) = \sum_{c=1}^{C} \pi_c \pi_{r|c} \frac{\exp\left[\sum_{i=1}^{I} \beta_{ixc}\right]}{\gamma_c(r)} \quad \text{Equation 7}$$

where $\pi_c$ denotes the mixing proportions for $c=1,\ldots,C$, and $\pi_{r|c}$ denotes the probabilities of latent score distribution for $r=0,\ldots,R_{max}$. For dichotomous items, the maximum score is $R_{max}=I$ if I denotes the number of items. In the general case, let $x_i \in \{0,\ldots,m_i\}$ be the i-th response variable, so that the maximum score for this item is $m_i$. The maximum number of raw scores is obviously $$R_{max} = \sum_{i=1}^{I} m_i$$

in that case and, if estimated without restrictions, the number of parameters for the latent score also is $R_{max}$ per latent class c.

There are a large number of different polytomous mixed Rasch models known in the art, including Andrich's (1988) rating scale model, the equidistance model (Andrich, 1982), Masters' partial credit model (1982), and a model suggested by Rost that combines features of the rating scale model and the equidistance model, using conditional maximum likelihood techniques. Further, there is a log-linear Rasch model (Kelderman, 1984). Further, there are various HYBRID models, such as Yamamoto's (1987, 1989). The HYBRID models expand the parameter space differently than other models. In contrast to the common practice of assuming that the same type of model should be used in all mixture components, Yamamoto's HYBRID model allows different models in different components of the mixture. This is useful for, e.g., studying speededness.

However, existing diagnostic models are not suitable for use in analyzing large scale survey data, such as data obtained in from the National Assessment of Educational Progress (NAEP), International Adult Literacy and Life Skills Survey (IASL), Trends in International Mathematics and Science Study (TIMSS) and Programme for International Student Assessment (PISA) surveys. These large scale surveys do not report on an individual examinee level. They are primarily concerned with group level (e.g., limited English proficiency (LEP) individuals (sometimes referred to as English language learners, or ELLS), or by gender). The assessments use many different test-forms, with only partial overlap. As a result, there is a lot of data missing by design. Data may also go missing inadvertently.

One factor assisting an IRT theorist is that large scale surveys are typically accompanied by observable background data on the makeup of the respondents.

Thus, there is a need for system and method for effectively recovering item parameters and population parameters from sparsely populated data sets without unacceptable levels of estimation error.

BRIEF DESCRIPTION OF DRAWINGS

In describing the preferred embodiments, reference is made to the accompanying figure, and wherein.

Figure 1:
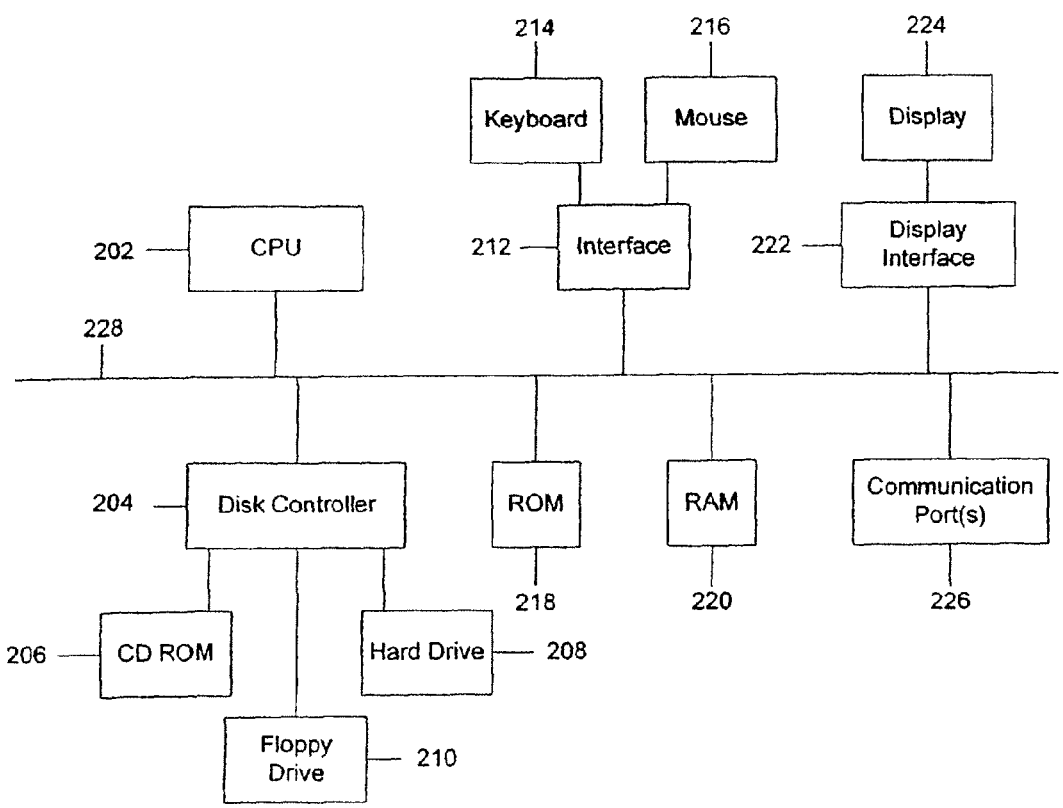
FIG. 1 is a block diagram of exemplary internal hardware that may be used to contain or implement the program instructions of a system embodiment.

It should be understood that the present invention is not limited to the preferred embodiments illustrated.

DETAILED DESCRIPTION OF THE INVENTION

Referring generally to FIG. 1, and upon review of this description, it will be appreciated that the apparatus of the present invention generally may be embodied within numerous configurations.

Disclosed herein is a general diagnostic model (GDM) that contains the LCA, the MRM, as well as other diagnostic models. A central building block of most models is often referred to as a Q-matrix, an I×K matrix that relates the I items to K skills, attributes, or dimensions. The entries $q_{ik}$ are integers in most cases, often $q_{ik} \in \{0,1\}$. The Q-matrix can be understood as the structural component of the model defining a hypothesis of which items require what combination of skills. A version of the GDM may be used to implement a multidimensional discrete version of the (mixture) generalized partial credit model. This model, pGDM, is therefore suitable for dichotomous and ordinal responses $x \in \{0,1,2,\ldots,m_i\}$. The pGDM contains 2PL and GPCM (M-)IRT, multiple classification latent class models, located latent class models, compensatory RUMs, and the Facet model. The model equation for a mixture version of the pGDM is:

$$P(X = x \mid \beta_i \ldots, a \ldots, q_i \ldots, c) = \frac{\exp\left[\beta_{xic} + \sum_{k=1}^{K} x\gamma_{ikc} q_{ik} a_k\right]}{1 + \sum_{y=1}^{m} \exp\left[\beta_{yic} + \sum_{k=1}^{K} y\gamma_{ikc} q_{ik} a_k\right]} \quad \text{Equation 8}$$

with c=1, . . . ,C groups, K attributes (e.g., distinct latent traits) a=(a$_1$, . . . ,a$_K$), latent class c and a dichotomous design Q-matrix (q$_{ik}$)$_{i=1 \ldots I, k=1 \ldots K}$. The $\beta_{ixc}$ are difficulty parameters and the x$\gamma_{ikc}$ term is a discrimination for skill k parameterized like it is done in the GPCM. The a$_k$ are discrete scores determined before estimation and can be chosen by the user. These scores are used to assign real numbers to the skill levels, for example a(0)=−1.0 and a(1)=1.0 may be chosen for dichotomous skills. For ordinal skills with s$_k$ levels, the a$_k$ may be defined using a(x)=x for x=0, . . . , (s$_k$−1) or a(0)=−s$_k$/2, . . . , a(s$_k$−1)=s$_k$/2. This pGDM can be used to estimate mixture versions of common IRT models such as the Rasch model, the 2PL model, and the generalized partial-credit model (GPCM), as well as multidimensional mixture versions of these models.

In mixture GDMs and multigroup GDMS (MG-GDMS), i.e., c>1, skill distributions may vary across groups, though the measurement model is the same for all items. Skill distributions may vary. Some items may be the same across groups. These items are called anchors, for obvious reasons. Other items may have different parameters in some groups. There further may be different skill distributions and separate calibration for all groups.

The difficulty in using existing diagnostic models on large scale survey data was described above. The primary issue is that data may be missing, often by design, though sometimes data may be missing inadvertently due to, for instance, loss of response data.

Further, observable background data collected in conjunction with a large scale survey may be aggregated and serve as grouping variables or auxiliary variables.

One example of a large scale survey is the IASL. The IASL is a large-scale assessment of adult literacy skills. Interviews for the IASL were conducted in 16 countries. The interviews included a set of background questionnaires and nine blocks of main assessment questions. The GDM may be applied to a subset of this data, the subset comprising 28 background items from seven countries.

The IASL items were split into two separate item sets. The first set includes 20 polytomous items about numeracy and literacy practices. An exemplary item of the first set is "How often do/did you read or use information from letters, memos or emails as part of your main job? Would you say at least once a week, less than once a week, rarely or never?" The second set includes 8 polytomous items about self-evaluation of numeracy and literacy abilities. An exemplary item of the second set is "Please tell me whether you strongly agree, agree, disagree or strongly disagree with the following statement: I have the reading skills in English I need to do my main job well." The GDM was applied to an IASL response set consisting of 48,360 samples. Most of the variables have missing values. When using the GDM to analyze the IASL data, the index of percentage increase in average log likelihood is used to assess model-data fit. A 2-class mixture 2PL model was found to best fit item set one, whereas a 3-class model was found to best fit item set two. The aggregated measures for item set one included the expectation of the posterior theta distribution (EAP) within the class of the highest estimated probability and the average of EAP in each class weighted by estimated class probabilities. The aggregated measure for item set two included the class number associated with the highest estimated class probability.

A further study was performed on simulated data. The set-up included 2,880 examinees, 36 items assessing up to four attributes. The Q-matrix was composed of zeroes and ones. The latent attributes were labeled as two levels, where zero is equivalent to non-mastery, and one is equivalent to mastery. The missing response rate was set alternatively at 10%, 25% and 50%, and responses were missing at random. Forty data sets for each missing response rate were generated according to GDM. The accuracy of the estimates may be summarized in the following table:

TABLE 1

|  |  | 10% missing | 25% missing | 50% missing |
|---|---|---|---|---|
| Item parameters | Average bias | 0.001 | 0.002 | 0.005 |
|  | Average RMSE | 0.071 | 0.083 | 0.119 |
| Population parameters | Average bias | 0.000 | 0.000 | 0.000 |
|  | Average RMSE | 0.004 | 0.004 | 0.007 |

As is apparent from the above, estimation of item difficulty and slope parameters deteriorate slightly with increased levels of missing data. However, skill distribution seems relatively unaffected, so that reporting group level results may be feasible even for extremely sparse data.

The NAEP grade 12 reading test is another large scale survey. The 2002 results are analyzed herein for illustrative purposes. The NAEP grade 12 reading test had three sub-scales: reading for literary experience; reading for gaining information; and reading to perform a task. There were 112 items in a balanced incomplete block (BIB) design, and 14,724 students participated by stratified sampling. A Q-matrix was postulated, where each sub-scale took on one attribute, and items only have loadings on the sub-scale to which they belong. Three models were used: a 2PL model; a 3-skill-3-level GDM with levels of −1.414, 0 and 1.414; and a 3-skill-4-level GDM with levels of −1.732, −0.5773, 0.5773 and 1.732. Under a single-group assumption, the following results were obtained, wherein the Bayesian information criterion is abbreviated as BIC:

TABLE 2

| Models | # of parameters | Log-likelihood | BIC |
|---|---|---|---|
| 2PL IRT | 328 | −150,234.69 | 303,617.3 |
| 3-skill-3-level GDM | 290 | −150,355.23 | 303,493.7 |
| 3-skill-4-level-GDM | 327 | −149,987.27 | 303,112.8 |

Under the multiple-group assumption, the following results were obtained:

TABLE 3

| Models | # of parameters | Log-likelihood | BIC |
|---|---|---|---|
| Racial Groups | 516 | −149,576.38 | 303,513 |
| Gender Groups | 390 | −149,701.72 | 302,699.2 |

Then, the GDM results were compared with the NAEP operational analysis for skills one through three, i.e., reading for literary experience; reading for gaining information; and reading to perform a task, respectively (wherein the name in parentheses is the software program used to generate the results):

TABLE 4

(skill one)

| Skill 1 | Mean (mdltm) | Mean (cgroup) | Diff. in mean | Std (mdltm) | Std (cgroup) |
|---|---|---|---|---|---|
| White | 0.1714 | 0.1764 | 0.0050 | 0.9436 | 0.9191 |
| Black | −0.5274 | −0.5240 | 0.0034 | 0.9420 | 0.9161 |
| Hispanic | −0.3936 | −0.4041 | −0.0105 | 1.0250 | 0.9913 |
| Asian | 0.0333 | 0.0209 | −0.0124 | 0.9806 | 0.9246 |

TABLE 5

(skill two)

| Skill 1 | Mean (mdltm) | Mean (cgroup) | Diff. in mean | Std (mdltm) | Std (cgroup) |
|---|---|---|---|---|---|
| White | 0.1494 | 0.1703 | 0.0209 | 0.9476 | 0.9198 |
| Black | −0.4253 | −0.4678 | 0.0425 | 0.8802 | 0.9058 |
| Hispanic | −0.3566 | −0.3965 | −0.0399 | 1.0124 | 0.9989 |
| Asian | −0.0107 | 0.0453 | −0.0345 | 0.9851 | 0.9097 |

TABLE 6

(skill three)

| Skill 1 | Mean (mdltm) | Mean (cgroup) | Diff. in mean | Std (mdltm) | Std (cgroup) |
|---|---|---|---|---|---|
| White | 0.1384 | 0.1536 | 0.0152 | 0.9674 | 0.9878 |
| Black | −0.4490 | −0.4866 | −0.0376 | 0.9267 | 0.9738 |
| Hispanic | −0.2778 | −0.2893 | −0.0115 | 1.0455 | 1.0900 |
| Asian | −0.0219 | −0.0715 | −0.0496 | 1.0694 | 1.0468 |

As the above tables show, both the simulation study and the cross-validation check show that the parameters can be recovered. The above tables also show that GDM is similar to the confirmatory factor analysis, which operates on categorical variables instead of continuous variables. Finally, the tables show that the single-group assumption versus the multiple-group assumption leads to different conclusions for certain subgroups, such as blacks and hispanics.

Another illustration of the use of the GDM in large scale surveys with sparse data sets is hereinafter disclosed. The NAEP mathematics 2005 grade 12 test has four sub-scales: number properties and operations; measurement and geometry; data analysis and probability; and algebra. Additionally, there are three complexity categories: low, moderate and high. The test comprises 180 items in a BIB design. 9,347 students took the test. A Q-matrix was postulated, wherein each sub-scale takes one attribute, and items only have loadings on the sub-scale to which they belong. Each complexity category is also taken as one attribute. Three models were used: 4-skill-4-level-GDM, with levels of −1.732, −0.05773, 0.5573 and 1.732; 7-skill-2-level GDM, with levels of −1.732 and 1.732; and 6-skill-2-level GDM, with levels of −1.732 and 1.732.

A single-group analysis was performed, as well as a cross-validation analysis, wherein the whole data set was randomly split into two data sets, of about 4,600 students, resulting in about 50% missing data. The single data set model resulted in the following:

TABLE 2

| Models | # of parameters | Log-likelihood | BIC |
|---|---|---|---|
| 4-skill-4-level GDM | 678 | −92,961.98 | 191,652.0 |
| 7-skill-2-level GDM | 730 | −92,783.83 | 191,735.1 |
| 6-skill-2-level-GDM | 632 | −93,531.19 | 192,401.8 |

The 7-skill-2-level GDM model was then used to analyze the sparse data sets. Out of 603 parameters, 452 parameter estimates had differences less than 0.1 across the two data sets. For each data set, the number students per parameter was approximately 7.5 Considering the small ratio and small differences in parameter estimates, the GDM model was able to recover the parameter estimates in this extremely sparse data.

FIG. 1 is a block diagram of exemplary internal hardware that may be used to contain or implement the program instructions of a system embodiment. Referring to FIG. 1, a bus 228 serves as the main information highway interconnecting the other illustrated components of the hardware. CPU 202 is the central processing unit of the system, performing calculations and logic operations required to execute a program. Read only memory (ROM) 218 and random access memory (RAM) 220 constitute exemplary memory devices.

A disk controller 204 interfaces with one or more optional disk drives to the system bus 228. These disk drives may be external or internal floppy disk drives such as 210, CD ROM drives 206, or external or internal hard drives 208. As indicated previously, these various disk drives and disk controllers are optional devices.

Program instructions may be stored in the ROM 218 and/or the RAM 220. Optionally, program instructions may be stored on a computer readable medium such as a floppy disk or a digital disk or other recording medium, a communications signal or a carrier wave.

An optional display interface 222 may permit information from the bus 228 to be displayed on the display 224 in audio, graphic or alphanumeric format. Communication with external devices may optionally occur using various communication ports 226. An exemplary communication port 226 may be attached to a communications network, such as the Internet or an intranet.

In addition to the standard computer-type components, the hardware may also include an interface 212 which allows for receipt of data from input devices such as a keyboard 214 or other input device 216 such as a remote control, pointer and/or joystick.

It should be appreciated that merely preferred embodiments of the invention have been described above. However, many modifications and variations to the preferred embodiments will be apparent to those skilled in the art, which will be within the spirit and scope of the invention. Therefore, the invention should not be limited to the described embodiments. To ascertain the full scope of the invention, the following claims should be referenced.

An embedded system may optionally be used to perform one, some or all of the operations of the present invention. Likewise, a multiprocessor system may optionally be used to perform one, some or all of the operations of the present invention.

It is to be understood that the invention is not limited in its application to the details of construction and to the arrangements of the components set forth in this description or illustrated in the drawings. The invention is capable of other embodiments and of being practiced and carried out in various ways. Hence, it is to be understood that the phraseology and terminology employed herein are for the purpose of description and should not be regarded as limiting.

As such, those skilled in the art will appreciate that the conception upon which this disclosure is based may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

What is claimed is:

1. A computer-implemented method of analyzing large scale survey results comprising:
    obtaining a sparse data set representing a subset of an original data set comprising a plurality of individuals' responses to a plurality of questions using a computer system, wherein the sparse data set comprises less than ninety percent of the responses in the original data set;
    analyzing the sparse data set using a diagnostic model using the computer system, the diagnostic model comprising multiple models according to an expression:

$$P(X = x \mid \beta_i \ldots, a \ldots, q_i \ldots, c) = \frac{\exp\left[\beta_{xic} + \sum_{k=1}^{K} x\gamma_{ikc} q_{ik} a_k\right]}{1 + \sum_{y=1}^{m} \exp\left[\beta_{yic} + \sum_{k=1}^{K} y\gamma_{ikc} q_{ik} a_k\right]},$$

wherein
        c is a number of observed groups ranging from 1 to an integer C,
        K is a number of attributes,
        $a_k$ are skill level parameters,
        i is an index for question items,
        $q_{ik}$ are parameters relating question items to skills,
        $\beta_{xic}$ and $\beta_{yic}$ are difficulty parameters for groups c=1, ..., C,
        x is an observed item response,
        m is a number of response categories, and
        $\gamma_{ikc}$ are discrimination parameters for skill k and for groups c=1, ..., C;
    said analyzing comprising generating a probability of given responses based upon difficulty parameters, skill levels, and parameters relating question items to skills; and
    obtaining, using the computer system, estimated person parameters indicative of an individual's ability as well as difficulty parameters and discrimination parameters, using the diagnostic model.

2. The method of claim 1, wherein the diagnostic model is constructed based on a Q-matrix;
    wherein the Q-matrix is a I×K matrix that relates I question items and K skills.

3. The method of claim 2, wherein the Q-matrix comprises values representing whether a particular combination of skills is required by a question item.

4. The method of claim 1, wherein the diagnostic model comprises a discrimination parameter for a particular skill.

5. The method of claim 1, wherein said analyzing further comprises generating the probability of given responses based upon a mixture of sub-populations.

6. The method of claim 1, wherein observable background data of the individuals are collected in conjunction with the original data set and incorporated into the diagnostic model as grouping variables.

7. A system for analyzing large scale survey results, the system comprising:
    a processing system;
    a processor-readable storage medium containing one or more programming instructions that, when executed, cause the processing system to execute steps comprising:
        obtaining a sparse data set representing a subset of an original data set comprising a plurality of individuals' responses to a plurality of questions, wherein the sparse data set comprises less than ninety percent of the responses in the original data set;
        analyzing the sparse data set using a diagnostic model, the diagnostic model comprising multiple models according to an expression:

$$P(X = x \mid \beta_i \ldots, a \ldots, q_i \ldots, c) = \frac{\exp\left[\beta_{xic} + \sum_{k=1}^{K} x\gamma_{ikc} q_{ik} a_k\right]}{1 + \sum_{y=1}^{m} \exp\left[\beta_{yic} + \sum_{k=1}^{K} y\gamma_{ikc} q_{ik} a_k\right]},$$

wherein
            c is a number of observed groups ranging from 1 to an integer C,
            K is a number of attributes,
            $a_k$ are skill level parameters,
            i is an index for question items,
            $q_{ik}$ are parameters relating question items to skills,
            $\beta_{xic}$ and $\beta_{yic}$ are difficulty parameters for groups c=1, ..., C,
            x is an observed item response,
            m is a number of response categories, and
            $\gamma_{ikc}$ are discrimination parameters for skill k and for groups c=1, ..., C;
        said analyzing comprising generating a probability of given responses based upon difficulty parameters, skill levels, and parameters relating question items to skills; and
        obtaining estimated person parameters indicative of an individual's ability as well as difficulty parameters and discrimination parameters, using the diagnostic model.

8. The system of claim 7, wherein the diagnostic model is constructed based on a Q-matrix;
    wherein the Q-matrix is a I×K matrix that relates to I question items and K skills.

9. The system of claim 8, wherein the Q-matrix comprises values representing whether a particular combination of skills is required by a question item.

10. The system of claim 7, wherein the diagnostic model comprises a discrimination parameter for a particular skill.

11. The system of claim 7, wherein said analyzing further comprises generating the probability of given responses based upon a mixture of sub-populations.

12. The system of claim 7, wherein observable background data of the individuals are collected in conjunction with the original data set and incorporated into the diagnostic model as grouping variables.

13. A non-transitory computer-readable storage medium for causing a computer system to carry out analyzing large scale survey results, said storage medium including programming instructions for causing the computer system to perform steps comprising:

obtaining a sparse data set representing a subset of an original data set comprising a plurality of individuals' responses to a plurality of questions, wherein the sparse data set comprises less than ninety percent of the responses in the original data set;

analyzing the sparse data set using a diagnostic model, the diagnostic model comprising multiple models according to an expression:

$$P(X = x \mid \beta_i \ldots, a \ldots, q_i \ldots, c) = \frac{\exp\left[\beta_{xic} + \sum_{k=1}^{K} x\gamma_{ikc} q_{ik} a_k\right]}{1 + \sum_{y=1}^{m} \exp\left[\beta_{yic} + \sum_{k=1}^{K} y\gamma_{ikc} q_{ik} a_k\right]},$$

wherein c is a number of observed groups ranging from 1 to an integer C,

K is a number of attributes, $a_k$ are skill level parameters, i is an index for question items, $q_{ik}$ are parameters relating question items to skills, $\beta_{xic}$ and $\beta_{yic}$ are difficulty parameters for groups c=1, ..., C, x is an observed item response, m is a number of response categories, and $\gamma_{ikc}$ are discrimination parameters for skill k and for groups c=1, ..., C;

said analyzing comprising generating a probability of given responses based upon difficulty parameters, skill levels, and parameters relating question items to skills; and obtaining estimated person parameters indicative of an individual's ability as well as difficulty parameters and discrimination parameters, using the diagnostic model.

14. The medium of claim 13, wherein the diagnostic model is constructed based on a Q-matrix;

wherein the Q-matrix is a I×K matrix that relates to I questions and K skills.

15. The medium of claim 14, wherein the Q-matrix comprises values representing whether a particular combination of skills is required by a question item.

16. The medium of claim 13, wherein the diagnostic model comprises a discrimination parameter for a particular skill.

17. The medium of claim 13, wherein said analyzing further comprises generating the probability of given responses based upon a mixture of sub-populations.

18. The medium of claim 13, wherein observable background data of the individuals are collected in conjunction with the original data set and incorporated into the diagnostic model as grouping variables.

* * * * *